US012029622B2

(12) United States Patent
Cheng et al.

(10) Patent No.: US 12,029,622 B2
(45) Date of Patent: Jul. 9, 2024

(54) ORAL-AREA POSITIONING DEVICE AND METHOD

(71) Applicant: Quanta Computer Inc., Taoyuan (TW)

(72) Inventors: Kai-Ju Cheng, Taoyuan (TW); Yu-Hsun Chen, Taoyuan (TW); Chin-Yuan Ting, Taoyuan (TW); Shao-Ang Chen, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 686 days.

(21) Appl. No.: 17/149,934

(22) Filed: Jan. 15, 2021

(65) Prior Publication Data

US 2022/0142739 A1 May 12, 2022

(30) Foreign Application Priority Data

Nov. 10, 2020 (TW) ................................ 109139094

(51) Int. Cl.
*G06K 9/00* (2022.01)
*A61C 7/00* (2006.01)
(Continued)

(52) U.S. Cl.
CPC ............. *A61C 7/002* (2013.01); *G06N 20/00* (2019.01); *G06T 7/73* (2017.01); *G06V 10/457* (2022.01);
(Continued)

(58) Field of Classification Search
CPC .................... G06N 20/00; A61C 7/002; G06T 2207/30036
See application file for complete search history.

(56) References Cited

U.S. PATENT DOCUMENTS

| 7,970,628 | B2 * | 6/2011 | Kuo | ....................... G16H 50/70 |
| | | | | 705/2 |
| 11,563,929 | B2 * | 1/2023 | Saphier | ................ A61C 9/0053 |
| 2020/0069042 | A1 * | 3/2020 | Masculo | ............ A46B 15/0002 |

FOREIGN PATENT DOCUMENTS

| CN | 111784754 A | * 10/2020 | ............. A61C 7/002 |
| CN | 111784754 A | 10/2020 | |

(Continued)

OTHER PUBLICATIONS

Jain, A. K., & Chen, H. (Mar. 2005). Registration of dental atlas to radiographs for human identification. In Biometric Technology for Human Identification II (vol. 5779, pp. 292-298). SPIE. (Year: 2005).*

(Continued)

*Primary Examiner* — Emily C Terrell
*Assistant Examiner* — Aidan Keup
(74) *Attorney, Agent, or Firm* — McClure, Qualey & Rodack, LLP (57) ABSTRACT

An oral-area positioning device is provided in the invention. The oral-area positioning device includes a storage circuit, a positioning circuit and a calculation circuit. The storage circuit stores information corresponding to a plurality of oral areas. The positioning circuit obtains a target image from an oral-image extracting device, and obtains a first position estimation result according to the information corresponding to the plurality of oral areas and a first algorithm. The positioning device obtains a second position estimation result at least according to the information corresponding to the plurality of oral areas, a second algorithm and a reference image position of a reference image, wherein the reference image position is one of the oral areas. The calculation circuit generates a third position estimation (Continued)

result according to the first position estimation result and the second position estimation result.

18 Claims, 5 Drawing Sheets

(51) Int. Cl.
*G06N 20/00* (2019.01)
*G06T 7/73* (2017.01)
*G06V 10/44* (2022.01)

(52) U.S. Cl.
CPC ............... *G06T 2207/20084* (2013.01); *G06T 2207/30036* (2013.01)

(56) References Cited

FOREIGN PATENT DOCUMENTS

| | | | |
|---|---|---|---|
| EP | 3 620 130 A1 | 3/2020 | |
| EP | 3620130 A1 * | 3/2020 | ........... A61B 5/0088 |
| WO | 2019/094504 A1 | 5/2019 | |

OTHER PUBLICATIONS

European Search Report dated Jul. 26, 2021, issued in application No. EP 21154968.8.
Cui, Z., et al.; "ToothNet: Automatic Tooth Instance Segmentation and Identification From Cone Beam CT Images;" 2019 IEEE/CVF Conference on Computer Vision and Pattern Recognition (CVPR); Jun. 2019; pp. 6361-6370.

* cited by examiner

ORAL-AREA POSITIONING DEVICE AND METHOD

CROSS REFERENCE TO RELATED APPLICATIONS

This application claims priority of TW Patent Application No. 109139094 filed on Nov. 10, 2020, the entirety of which is incorporated by reference herein.

BACKGROUND OF THE INVENTION

Field of the Invention

The invention generally relates to oral-area positioning technology, and more particularly, to an oral-area positioning technology in which the Hidden Markov Model (HMM) algorithm is applied to the oral-area positioning.

Description of the Related Art

As technology has progressed, oral-area positioning is being applied more widely. The result of oral-area positioning can be used to construct an image of whole oral cavity of the patient, which allows the doctor to know the condition of the patient's teeth more clearly using the constructed image.

Therefore, how to generate an oral-area positioning result more accurately is a subject that is worthy of discussion.

BRIEF SUMMARY OF THE INVENTION

An oral-area positioning device and method are provided to overcome the problems mentioned above.

An embodiment of the invention provides an oral-area positioning device. The oral-area positioning device includes a storage circuit, a positioning circuit and a calculation circuit. The storage circuit stores information corresponding to a plurality of oral areas.

The positioning circuit is coupled to the storage circuit. The positioning circuit obtains a target image from an oral-image extracting device, and obtains a first position estimation result according to the information corresponding to the oral areas and a first algorithm. The positioning device obtains a second position estimation result at least according to the information corresponding to the oral areas, a second algorithm and a reference image position of a reference image, wherein the reference image position is one of the oral areas. The calculation circuit is coupled to the positioning circuit. The calculation circuit generates a third position estimation result according to the first position estimation result and the second position estimation result.

According to an embodiment of the invention, the information corresponding to the oral areas comprises the machine learning result of each oral area, feature information of each oral area and/or inertial measurement unit (IMU) information of each oral area.

According to an embodiment of the invention, the first algorithm is a deep learning algorithm, an image comparison algorithm or an IMU algorithm.

According to an embodiment of the invention, the second algorithm is a Hidden Markov Model (HMM) algorithm.

According to an embodiment of the invention, the information corresponding to the oral areas further comprises moving probabilities between the oral areas, and the positioning circuit uses the second algorithm to obtain the second position estimation result according to the moving probabilities between the oral areas and the reference image position.

According to an embodiment of the invention, the information corresponding to the oral areas further comprises distance information between the oral areas or angle information between the oral areas. According to an embodiment of the invention, the positioning circuit obtains shift information between the target image and the reference image according to a third algorithm, and the positioning circuit uses the second algorithm to obtain the second position estimation result according to the distance information between the oral areas, the reference image position and the shift information, wherein the third algorithm is an image comparison algorithm or an IMU algorithm. According to another embodiment of the invention, the positioning circuit obtains angle variance information between the target image and the reference image according to a fourth algorithm, and the positioning circuit uses the second algorithm to obtain the second position estimation result according to the angle information between the oral areas, the reference image position and the angle variance information, wherein the fourth algorithm is an IMU algorithm.

According to an embodiment of the invention, the calculation circuit multiplies the first position estimation result by the second position estimation result to generate the third position estimation result.

According to an embodiment of the invention, the calculation circuit multiplies the first position estimation result by a first weight to generate a first result, and multiplies the second position estimation result by a second weight to generate a second result, and the calculation circuit adds the first result to the second result to generate the third position estimation result.

An embodiment of the invention provides an oral-area positioning method. The oral-area positioning method is applied to an oral-area positioning device. The oral-area positioning method comprises the steps of obtaining a target image from an oral-image extracting device; obtaining a first position estimation result according to information corresponding to the oral areas and a first algorithm; obtaining a second position estimation result at least according to the information corresponding to the oral areas, a second algorithm and a reference image position of a reference image, wherein the reference image position is one of the oral areas; and generating a third position estimation result according to the first position estimation result and the second position estimation result.

Other aspects and features of the invention will become apparent to those with ordinary skill in the art upon review of the following descriptions of specific embodiments of an oral-area positioning device and method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
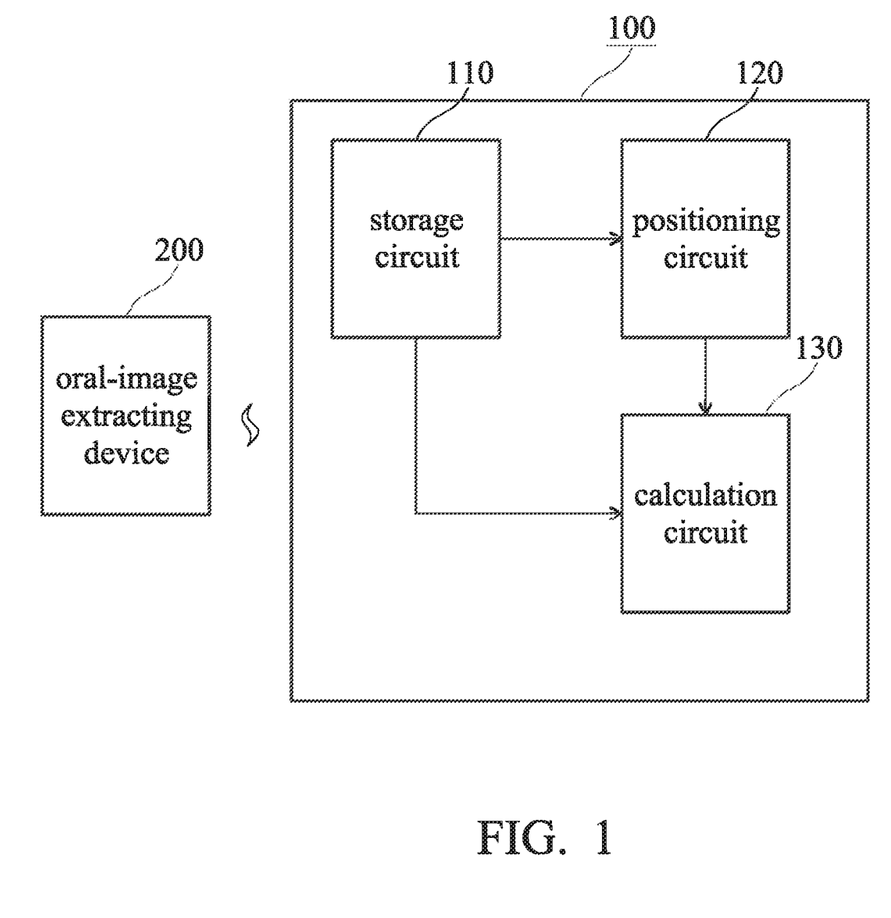
FIG. 1 is a block diagram of an oral-area positioning device 100 according to an embodiment of the invention.

FIG. 1 is a block diagram of an oral-area positioning device 100 according to an embodiment of the invention. As shown in FIG. 1, the oral-area positioning device 100 may comprise a storage device 110, a positioning circuit 120 and a calculation circuit 130. It should be noted that FIG. 1 presents a simplified block diagram in which only the elements relevant to the invention are shown. However, the invention should not be limited to what is shown in FIG. 1. The oral-area positioning device 100 may also comprise other elements and the connections between the elements may be different from the oral-area positioning device 100. According to an embodiment of the invention, the positioning circuit 120 and the calculation circuit 130 may be integrated in a single chip or module. In another embodiment, the storage device 110, the positioning circuit 120 and the calculation circuit 130 may also be integrated in a single chip or module.

According to the embodiments of the invention, the storage device 110 may be a volatile memory (e.g. Random Access Memory (RAM)), or a non-volatile memory (e.g. flash memory, Read Only Memory (ROM)), a hard disk, or a combination of the above memory devices. The storage circuit 110 may store the required files and data for the oral-area positioning, e.g. the information corresponding to a plurality of areas of the oral cavity.

Figure 2:
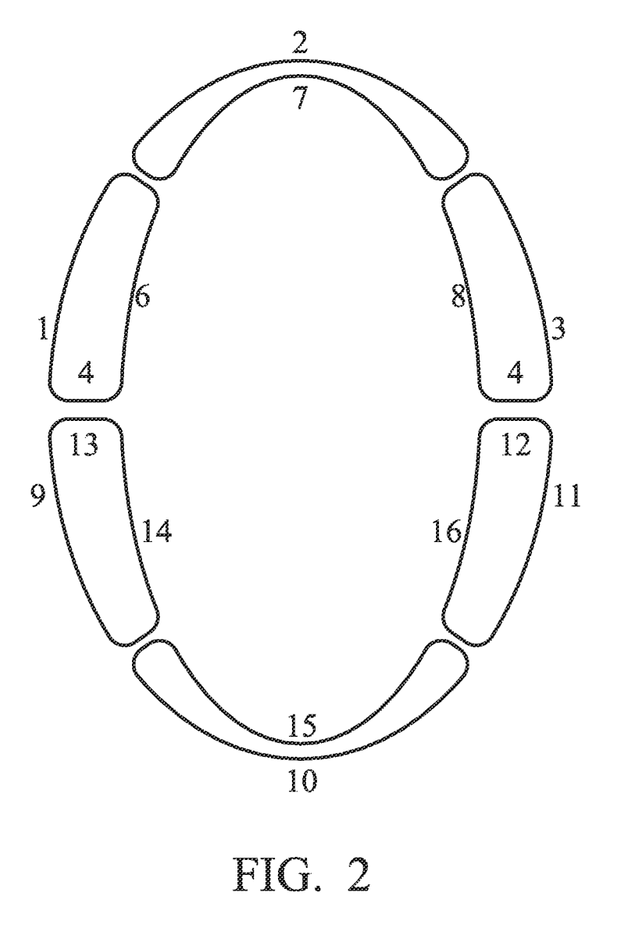
FIG. 2 is a schematic diagram of a plurality of oral areas according to an embodiment of the invention.

According to the embodiments of the invention, the oral cavity may be divided into a plurality of areas (i.e. oral areas) in advance, and the information of each area may store in the storage circuit 110 previously. As shown in FIG. 2, the oral cavity is divided into 16 areas previously, but the invention should not be limited thereto. According to an embodiment of the invention, the information corresponding to each area may be the machine learning result corresponding to each area, wherein the machine learning result corresponding to each area is generated after image data of each area has been trained through a deep learning algorithm. According to another embodiment of the invention, the information corresponding to each area may be the (image) information contained in the dental image corresponding to each area. According to another embodiment of the invention, the information corresponding to each area may be the inertial measurement unit (IMU) information (e.g. the position (or orientation) and angle information corresponding to the teeth of each area) corresponding to each area. According the embodiments of the invention, the information of each area stored in the storage circuit 110 may comprise the information of one or more of the above embodiments, but the invention should not be limited thereto.

According to an embodiment of the invention, when the oral-area positioning is performed, the oral-area positioning circuit 100 may obtain a target image from an oral-image extracting device 200 to estimate the oral area corresponding to the target image, wherein the target image is the oral image extracted or captured by the oral-image extracting device 200 at the current time point. According to the embodiments of the invention, at different time points, the oral-image extracting device 200 may be moved to different positions of the oral cavity to extract the oral images corresponding to different oral areas.

According to an embodiment, the oral-image extracting device 200 may be a dental camera (or teeth camera) device, but the invention should not be limited thereto. According to an embodiment of the invention the oral-image extracting device 200 may comprise an IMU to generate the IMU information (e.g. the position and angle information) when the oral-image extracting device 200 extracts the target image.

According to an embodiment, the oral-image extracting device 200 may transmit the extracted oral images and/or IMU information to the oral-area positioning device 100 through a wireless communication method, e.g. Bluetooth, Wi-Fi or mobile communication (cellular network), but the invention should not be limited thereto. The purpose of the invention is determining which area the extracted oral image corresponds to.

According to an embodiment of the invention, after the oral-area positioning device 100 obtains the target image from the oral-image extracting device 200, the positioning circuit 120 of the oral-area positioning device 100 may determine which oral area the target image corresponds to, based on a first algorithm and the information corresponding to each oral area stored in the storage circuit 110, and generate a first position estimation result.

According to an embodiment of the invention, the first algorithm may be a deep learning algorithm. In the embodiment, the positioning circuit 120 may determine which oral area the target image corresponds to, based on the deep learning algorithm and the information corresponding to each oral area (i.e. the machine learning result corresponding to each oral area) stored in the storage circuit 110, and generate the first position estimation result. Specifically, the positioning circuit 120 may input the target image to a deep learning model which has been trained to estimate the oral area corresponding to the target image, i.e. the first position estimation result is the estimated oral area corresponding to the target image.

According to another embodiment of the invention, the first algorithm may be an image comparison algorithm. In the embodiment, the positioning circuit 120 may determine which oral area the target image corresponds to, based on the image comparison algorithm and the information corresponding to each oral area (i.e. the information contained in the dental image corresponding to each oral area) stored in the storage circuit 110, and generate the first position estimation result. Specifically, the positioning circuit 120 may compare the features of the target image with the features of the previously stored dental image corresponding to each oral area in order to find the oral area corresponding to the dental image which is the most similar to the target image, i.e. the first position estimation result is the oral area corresponding to the dental image which is the most similar to the target image.

According to another embodiment of the invention, the first algorithm may be an IMU algorithm. In the embodiment, the positioning circuit 120 may determine which oral area the target image corresponds to, based on the IMU algorithm and the information corresponding to each oral area (i.e. the IMU information corresponding to each oral area) stored in the storage circuit 110, and generate the first position estimation result. Specifically, the positioning circuit 120 may compare the IMU information of the target image with the IMU information of the previously stored dental image corresponding to each oral area to find the oral area corresponding to the dental image which is the most similar to the target image, i.e. the first position estimation result is the oral area corresponding to the dental image which is the most similar to the target image.

According to an embodiment of the invention, after the first position estimation result has been generated, the positioning circuit 120 may obtain a second position estimation result according to the information corresponding to the oral areas, a second algorithm and a reference image position of a reference image. According to an embodiment of the invention, comparing with the target image at the current time point, the reference image can be regarded as a target image at a previous time point, and the reference image position may be one of the oral areas. For example, the reference image may be the target image at time point t−1 and its reference image position (i.e. one oral area) may be known (e.g. the reference image position has been estimated). Therefore, the reference image and the reference image position can be used to estimate the oral area corresponding to the target image at the current time point t (i.e. estimate the oral-image extracting device 200 moving from the reference image position (i.e. one oral area) to which oral area during the time point t−1 to the current time point t). According to an embodiment of the invention, the second algorithm may be the Hidden Markov Model (HMM) algorithm. Below different embodiments will be used to illustrate how the positioning circuit 120 generating the second position estimation result corresponding to the target image through the second algorithm (i.e. HMM algorithm).

Figure 3:
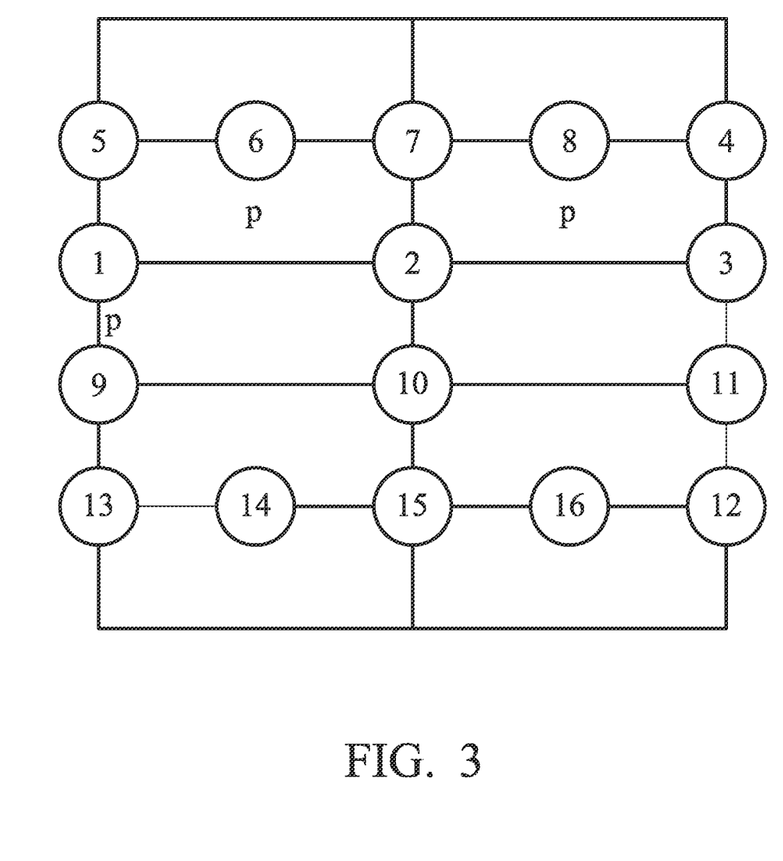
FIG. 3 is a schematic diagram of the moving probabilities between the oral areas according to an embodiment of the invention.

According to an embodiment of the invention for second algorithm, the information corresponding to each oral area stored in the storage circuit 110 may further comprise the moving probabilities between each oral area. Specifically, the moving probability between each area means the probability of the oral-image extracting device 200 moving from one oral area to another oral area when the oral-image extracting device 200 extracts the oral images during continuous time points. Taking FIG. 3 for example, FIG. 3 is a schematic diagram of the moving probabilities between the oral areas 1~16 shown in FIG. 2. As shown in FIG. 3, moving probability between the adjacent oral areas is p. For example, the moving probability from the oral area 1 to the oral area 2 is p, and the moving probability from the oral area 2 to the oral area 3 is p. In addition, as shown in FIG. 3, the moving probability between the non-adjacent oral areas is the power of the shortest path between the non-adjacent oral areas (i.e. p the shortest path). For example, the moving probability from the oral area 1 to the oral area 8 is p3, and the moving probability from the oral area 3 to the oral area 10 is p2. The positioning circuit 120 may use the second algorithm (i.e. HMM algorithm) to obtain the second position estimation result according to the moving probabilities between each oral area and the reference image position (i.e. one oral area). Specifically, the positioning circuit 120 may estimate the moving probabilities between the reference image position and other oral areas to select the oral area with the highest moving probability as the second position estimation result.

According to another embodiment of the invention for second algorithm, the information corresponding to each oral area stored in the storage circuit 110 may further comprise the distance information between each oral area. Specifically, the distance $Z_{i,j}$ between each oral area may be measured in advance, wherein the distance $Z_{i,j}$ means the distance of moving from the oral area i to the oral area j along the tooth contour. Taking FIG. 2 for example, the distance $Z_{1,2}$ means the distance of moving from the oral area 1 to the oral area 2 along the tooth contour, and the distance $Z_{15,16}$ means the distance of moving from the oral area 15 to the oral area 16 along the tooth contour. In addition, in the embodiment, the positioning circuit 120 may obtain shift information between the target image and the reference image according to a third algorithm.

In an embodiment, the third algorithm may be an image comparison algorithm (e.g. the feature comparison algorithm). In the embodiment, the positioning circuit 120 may compare the features of the target image with the features of the reference image to calculate the shift pixels of the features. After the positioning circuit 120 obtains the shift pixels, the positioning circuit 120 may estimate the distance variance d (i.e. the shift information) between the target image and the reference image according to the proportional relation between the pixel and the distance.

In another embodiment, the third algorithm may be an IMU algorithm. In the embodiment, the positioning circuit 120 may obtain the acceleration variance and the time variance between the target image and the reference image according to the IMU information of the target image and the IMU information of the reference image. Then, the positioning circuit may estimate the distance variance d (i.e. the shift information) between the target image and the reference image according to the acceleration variance and the time variance.

Figure 4:
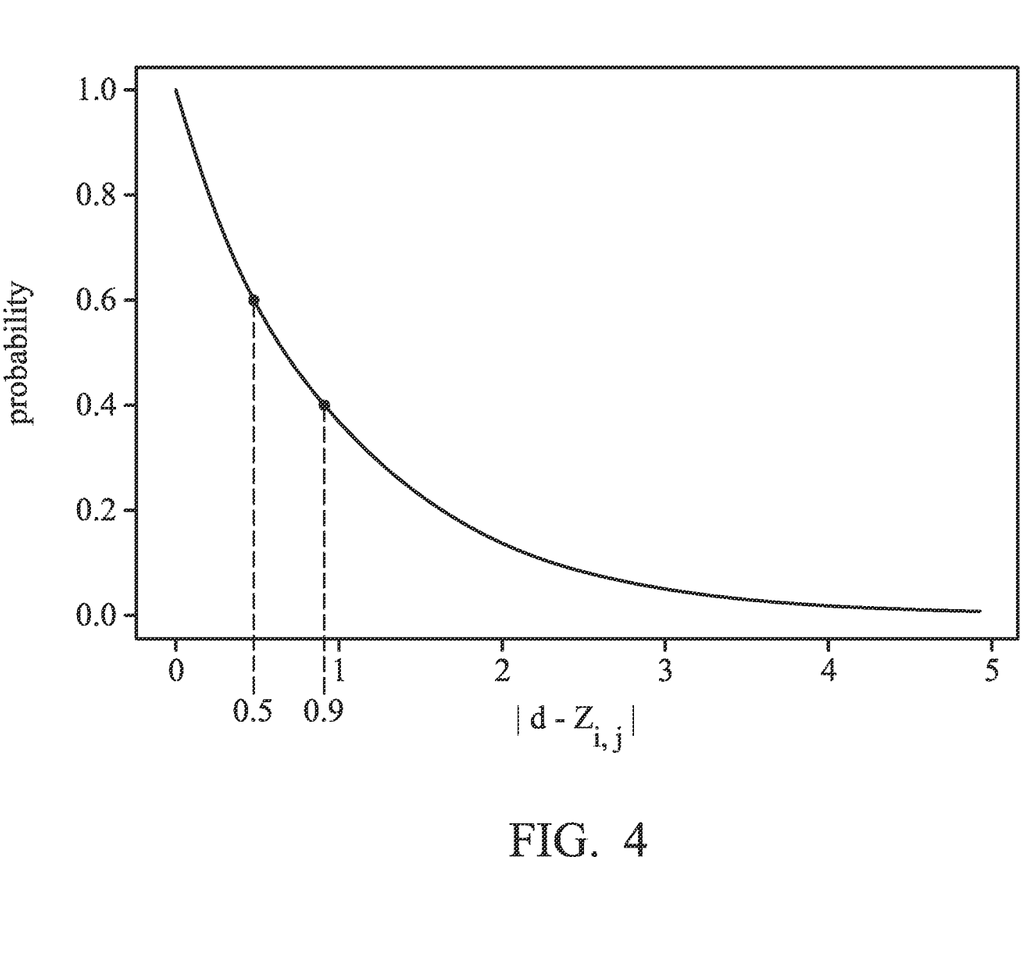
FIG. 4 is a distribution diagram of a probability density function according to an embodiment of the invention.

Then, the positioning circuit 120 may use the second algorithm (i.e. HMM algorithm) to obtain the second position estimation result corresponding to the target image according to the distance information (i.e. $Z_{i,j}$) between each oral area, the reference image position (i.e. the oral area i) and the shift information (i.e. the distance variance d) between the target image and the reference image. Specifically, the positioning circuit 120 may substitute the difference of the distance variance d and the distance information $Z_{i,j}$ (i.e. $|d-Z_{i,j}|$) into a probability density function to generate a distribution diagram (i.e. the second position estimation result). For example, the positioning circuit 120 may substitute the difference of the distance variance d and the distance information $Z_{i,j}$ (i.e. $|d-Z_{i,j}|$) into an exponential distribution function:

$$f(x;\lambda) = \begin{cases} \lambda e^{-\lambda x}, & x \geq 0 \\ 0, & x < 0 \end{cases},$$

Wherein the positioning circuit 120 may regard the difference of the distance variance d and the distance information $Z_{i,j}$ (i.e. $|d-Z_{i,j}|$) as the input x of the exponential distribution function. In the embodiment, when the difference of the distance variance d and the distance information $Z_{i,j}$ (i.e. $|d-Z_{i,j}|$) is smaller, it means that the probability of moving from the oral area i (i.e. the reference image position) to the oral area j (i.e. the possible position corresponding to the target image) is higher. Taking FIG. 4 for example, when the difference of the variance d and the distance information $Z_{i,j}$ (i.e. $|d-Z_{i,j}|$) is 0.5, probability is 60%, and the difference of the of the variance d and the distance information $Z_{i,j}$ (i.e. $|d-Z_{i,j}|$) is 0.9, the probability is 40%. Therefore, the positioning circuit 120 may estimation the probability corresponding to each oral area for the target image to select the oral area with the highest probability as the second position estimation result.

According to another embodiment of the invention for second algorithm, the information corresponding to each oral area stored in the storage circuit 110 may further comprise the angle information between each oral area. Specifically, the angle ri,j between each oral area may be measured in advance, wherein the angle ri,j means the angle of moving from the oral area i to the oral area j along the tooth contour. Taking FIG. 2 for example, the angle r1,2 means the angle of moving from the oral area 1 to the oral area 2 along the tooth contour, and the angle r15,16 means the distance of moving from the oral area 15 to the oral area 16 along the tooth contour. In addition, in the embodiment, the positioning circuit 120 may obtain angle variation information between the target image and the reference image according to a fourth algorithm.

In an embodiment, the fourth algorithm may be an IMU algorithm. In the embodiment, the positioning circuit 120 may obtain the acceleration variance and the time variance between the target image and the reference image according to the IMU information of the target image and the IMU information of the reference image. Then, the positioning circuit 120 may estimate the rotation angle variance c (i.e. the angle variation information) between the target image and the reference image according to the acceleration variance and the time variance.

Then, the positioning circuit 120 may use the second algorithm (i.e. HMM algorithm) to obtain the second position estimation result corresponding to the target image according to the angle information (i.e. $r_{i,j}$) between each oral area, the reference image position (i.e. the oral area i) and the angle variance information (i.e. the rotation angle variance c) between the target image and the reference image. Specifically, the positioning circuit 120 may substitute the difference of the rotation angle variance c and the angle information $r_{i,j}$ (i.e. $|c-r_{i,j}|$) into a probability density function to generate a distribution diagram (i.e. the second position estimation result). For example, the positioning circuit 120 may substitute the difference of the rotation angle variance c and the angle information $r_{i,j}$ (i.e. $|c-r_{i,j}|$) into an exponential distribution function:

$$f(x;\lambda) = \begin{cases} \lambda e^{-\lambda x}, & x \geq 0 \\ 0, & x < 0 \end{cases},$$

wherein the positioning circuit 120 may regard the difference of the rotation angle variance c and the angle information $r_{i,j}$ (i.e. $|c-r_{i,j}|$) as the input x of the exponential distribution function. In the embodiment, when the difference of the rotation angle variance c and the angle information $r_{i,j}$ (i.e. $|c-r_{i,j}|$) is smaller, it means that the probability of moving from the oral area i (i.e. the reference image position) to the oral area j (i.e. the possible position corresponding to the target image) is higher. Therefore, the positioning circuit 120 may estimation the probability corresponding to each oral area for the target image to select the oral area with the highest probability as the second position estimation result.

The calculation circuit 130 may obtain the first position estimation result and the second position estimation result.

According to an embodiment of the invention, the calculation circuit 130 may generate a third position estimation result corresponding to the target image according to the first position estimation result and the second position estimation result, so as to determine the oral area corresponding to the target image. According to an embodiment of the invention, the calculation circuit 130 may multiply the first position estimation result by the second position estimation result to generate the third position estimation result. For example, it is assumed that the reference image position is the oral area 1. When the calculation circuit 130 obtains the probability of the target image corresponding to the oral area 2 (i.e. the probability of the oral-image extracting device 200 moving from the oral area 1 to the oral area 2 during the previous time point to the current time point) is 40% and the probability of the target image corresponding to the oral area 3 (i.e. the probability of the oral-image extracting device 200 moving from the oral area 1 to the oral area 3 during the previous time point to the current time point) is 30% according to the first position estimation result, and obtains the probability of the target image corresponding to the oral area 2 is 60% and the probability of the target image corresponding to the oral area 3 is 40% according to the second position estimation result, the calculation circuit 130 may multiply the first position estimation result by the second position estimation result to generate the third position estimation result. That is to say, in the third position estimation result, the probability of the target image corresponding to the oral area 2 is 24% (40%*60%) and the probability of the target image corresponding to the oral area 3 is 12% (30%*40%). Therefore, the user may determine that the target image corresponds to oral area 2 (i.e. the oral-image extracting device 200 moves from the oral area 1 to the oral area 2 during the previous time point to the current time point) according to the third position estimation result. It should be noted that the above example is only used to illustrate the embodiment of the invention, but the invention should not be limited thereto.

According to another embodiment of the invention, the calculation circuit 130 may multiply the first position estimation result by a first weight to generate a first result, and multiply the second position estimation result by a second weight to generate a second result. Then, the calculation circuit 130 may add the first result to the second result. For example, it is assumed that the reference image position is the oral area 1, the first weight corresponding to the first position estimation result is 40%, and the second weight corresponding to the second position estimation result is 60%. When the calculation circuit 130 obtains the probability of the target image corresponding to the oral area 2 (i.e. the probability of the oral-image extracting device 200 moving from the oral area 1 to the oral area 2 during the previous time point to the current time point) is 40% and the probability of the target image corresponding to the oral area 3 (i.e. the probability of the oral-image extracting device 200 moving from the oral area 1 to the oral area 3 during the previous time point to the current time point) is 30% according to the first position estimation result, and obtains the probability of the target image corresponding to the oral area 2 is 60% and the probability of the target image corresponding to the oral area 3 is 40% according to the second position estimation result, in the third position estimation result, the probability of the target image corresponding to the oral area 2 is 52% (40%*40%+60%*60%=52%), and the probability of the target image corresponding to the oral area 3 is 36% (30%*40%+40%*60%=36%). Therefore, the user may determine that the target image corresponds to oral area 2 (i.e. the oral-image extracting device 200 moves from the oral area 1 to the oral area 2 during the previous time point to the current time point) according to the third position estimation result. It should be noted that the above example is only used to illustrate the embodiment of the invention, but the invention should not be limited thereto.

Because the oral-area positioning device 100 provided in the embodiments of the invention performs two estimations, the oral-area positioning device 100 may determine the oral area corresponding to the target image at the current point more accurately.

Figure 5:
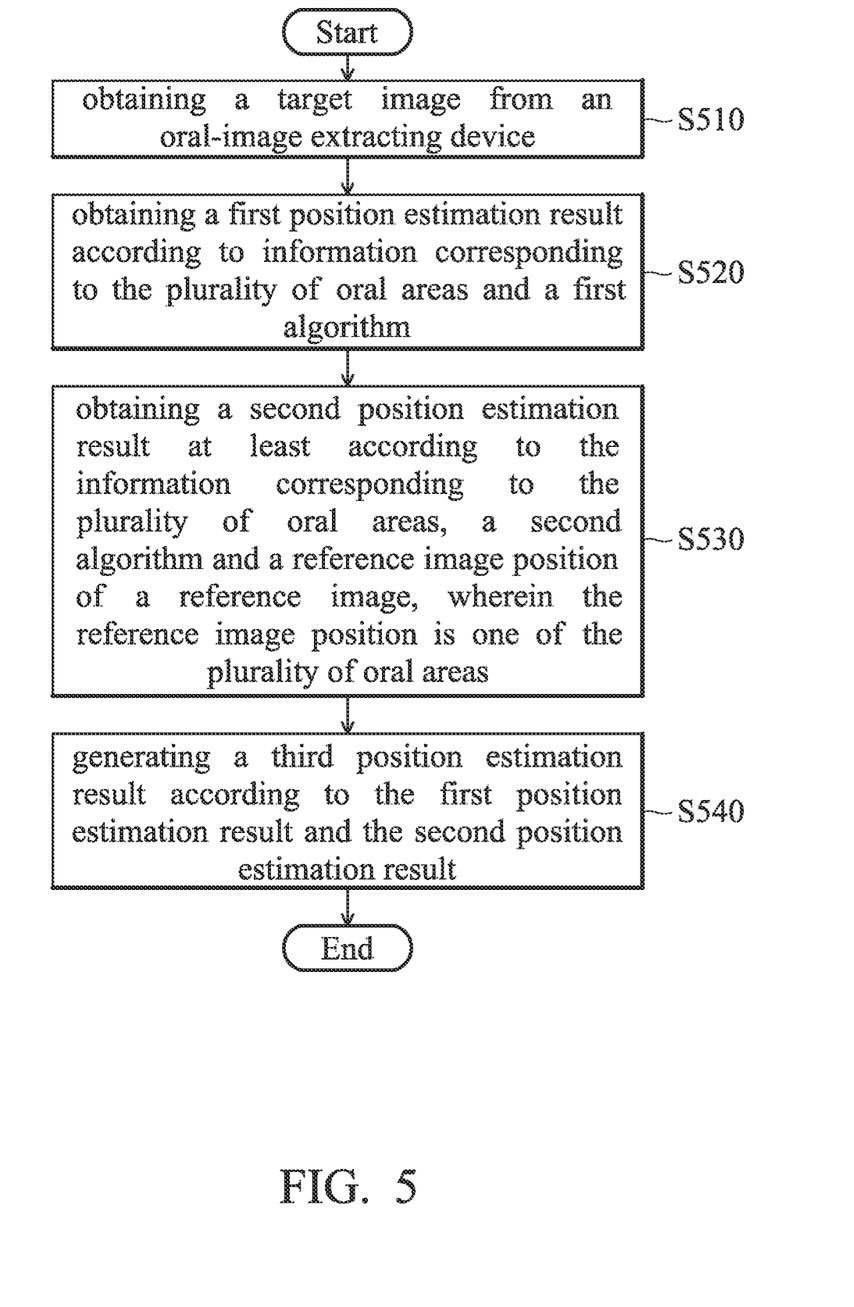
FIG. 5 is a flow chart illustrating an oral-area positioning method according to an embodiment of the invention.

FIG. 5 is a flow chart illustrating an oral-area positioning method according to an embodiment of the invention. The oral-area positioning method can be applied to the oral-area positioning device 100. As shown in FIG. 5, in step S510, a positioning circuit of the oral-area positioning device 100 obtains a target image from an oral-image extracting device 200.

In step S520, the positioning circuit of the oral-area positioning device 100 obtains a first position estimation result according to the information corresponding to a plurality of oral areas and a first algorithm.

In step S530, the positioning circuit of the oral-area positioning device 100 obtains a second position estimation result at least according to the information corresponding to the oral areas, a second algorithm and a reference image position (e.g. one oral area) of a reference image, wherein the reference image position is one of the oral areas.

In step S540, the calculation circuit of the oral-area positioning device 100 generates a third position estimation result corresponding to the target image according to the first position estimation result and the second position estimation result.

According to an embodiment of the invention, in the oral-area positioning method, the information corresponding to the oral areas comprises the machine learning result of each oral area, feature information of each oral area and/or inertial measurement unit (IMU) information of each oral area.

According to an embodiment of the invention, in the oral-area positioning method, the first algorithm may be a deep learning algorithm, an image comparison algorithm or an IMU algorithm.

According to an embodiment of the invention, in the oral-area positioning method, the second algorithm may be a Hidden Markov Model (HMM) algorithm.

According to an embodiment of the invention, in the oral-area positioning method, the information corresponding to the oral areas further comprises the moving probabilities between the oral areas. In the embodiment, step S530 may further comprises that the positioning circuit of the oral-area positioning device 100 uses the second algorithm to obtain the second position estimation result according to the moving probabilities between the oral areas and the reference image position.

According to an embodiment of the invention, in the oral-area positioning method, the information corresponding to the oral areas further comprises distance information between the oral areas. In the embodiment, step S530 may further comprises that the positioning circuit of the oral-area positioning device 100 obtains shift information between the target image and the reference image according to a third algorithm, and the positioning circuit of the oral-area positioning device 100 uses the second algorithm to obtain the second position estimation result according to the distance information between the oral areas, the reference image position and the shift information. In the embodiment, the third algorithm may be an image comparison algorithm or an IMU algorithm.

According to an embodiment of the invention, in the oral-area positioning method, the information corresponding to the oral areas further comprises angle information between the oral areas. In the embodiment, step S530 may further comprises that the positioning circuit of the oral-area positioning device 100 obtains angle variance information between the target image and the reference image according to a fourth algorithm, and the positioning circuit of the oral-area positioning device 100 uses the second algorithm to obtain the second position estimation result according to the angle information between the oral areas, the reference image position and the angle variance information. In the embodiment, the fourth algorithm may be an IMU algorithm.

In an embodiment of the invention, in the oral-area positioning method, step S540 may further comprise that the calculation circuit of the oral-area positioning device 100 may multiply the first position estimation result by the second position estimation result to generate the third position estimation result.

In an embodiment of the invention, in the oral-area positioning method, step S540 may further comprise that the calculation circuit of the oral-area positioning device 100 may multiply the first position estimation result by a first weight to generate a first result, and multiply the second position estimation result by a second weight to generate a second result. Then, the calculation circuit of the oral-area positioning device 100 may add the first result to the second result to generate the third position estimation result.

According to the oral-area positioning method provided in the invention, the oral-area positioning device 100 can use the position estimation result generated based on the HMM algorithm to optimize the position estimation result generated based on the first algorithm, and perform calculation to the two position estimation results to generate more accurate position estimation result.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor can read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects. Obviously, the teaching of the invention can be accomplished by many methods, and any specific configurations or functions in the disclosed embodiments only present a representative condition. Those who are skilled in this technology will understand that all of the disclosed aspects in the invention can be applied independently or be incorporated.

While the invention has been described by way of example and in terms of preferred embodiment, it should be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. An oral-area positioning device, comprising:
a storage circuit, storing information corresponding to a plurality of oral areas;
a positioning circuit, coupled to the storage circuit, obtaining a target image from an oral-image extracting device at a current time point, and obtaining a first position estimation result corresponding to the target image according to the information corresponding to the plurality of oral areas and a first algorithm, wherein the positioning device obtains a second position estimation result corresponding to the target image at least according to the information corresponding to the plurality of oral areas, a second algorithm and a reference image position of a reference image, wherein the reference image position is one of the plurality of oral areas and the second algorithm is a Hidden Markov Model (HMM) algorithm, and wherein the reference image is a previous target image at a previous time point; and
a calculation circuit, coupled to the positioning circuit and generating a third position estimation result corresponding to the target image according to the first position estimation result and the second position estimation result.

2. The oral-area positioning device of claim 1, wherein the information corresponding to the plurality of oral areas comprises a machine learning result of each oral area, feature information of each oral area and/or inertial measurement unit (IMU) information of each oral area.

3. The oral-area positioning device of claim 1, wherein the first algorithm is a deep learning algorithm, an image comparison algorithm or an IMU algorithm.

4. The oral-area positioning device of claim 1, wherein the information corresponding to the plurality of oral areas further comprises moving probabilities between the oral areas, and the positioning circuit uses the second algorithm to obtain the second position estimation result according to the moving probabilities between the oral areas and the reference image position.

5. The oral-area positioning device of claim 1, wherein the information corresponding to the plurality of oral areas further comprises distance information between the oral areas or angle information between the oral areas.

6. The oral-area positioning device of claim 5, wherein the positioning circuit obtains shift information between the target image and the reference image according to a third algorithm, and the positioning circuit uses the second algorithm to obtain the second position estimation result according to the distance information between the oral areas, the reference image position and the shift information, wherein the third algorithm is an image comparison algorithm or an IMU algorithm.

7. The oral-area positioning device of claim 5, wherein the positioning circuit obtains angle variance information between the target image and the reference image according to a fourth algorithm, and the positioning circuit uses the second algorithm to obtain the second position estimation result according to the angle information between the oral areas, the reference image position and the angle variance information, wherein the fourth algorithm is an IMU algorithm.

8. The oral-area positioning device of claim 1, wherein the calculation circuit multiplies the first position estimation result by the second position estimation result to generate the third position estimation result.

9. The oral-area positioning device of claim 1, wherein the calculation circuit multiplies the first position estimation result by a first weight to generate a first result, and multiplies the second position estimation result by a second weight to generate a second result, and the calculation circuit adds the first result to the second result to generate the third position estimation result.

10. An oral-area positioning method, applied to an oral-area positioning device, comprising:
obtaining, by a positioning circuit of the oral-area positioning device, a target image from an oral-image extracting device at a current time point;
obtaining, by the positioning circuit, a first position estimation result corresponding to the target image according to information corresponding to a plurality of oral areas and a first algorithm;
obtaining, by the positioning circuit, a second position estimation result corresponding to the target image at least according to the information corresponding to the plurality of oral areas, a second algorithm and a reference image position of a reference image, wherein the reference image position is one of the plurality of oral areas and the second algorithm is a Hidden Markov Model (HMM) algorithm, and wherein the reference image is a previous target image at a previous time point; and
generating, by a calculation circuit of the oral-area positioning device, a third position estimation result corresponding to the target image according to the first position estimation result and the second position estimation result.

11. The oral-area positioning method of claim 10, wherein the information corresponding to the plurality of oral areas comprises a machine learning result of each oral area, feature information of each oral area and/or inertial measurement unit (IMU) information of each oral area.

12. The oral-area positioning method of claim 10, wherein the first algorithm is a deep learning algorithm, an image comparison algorithm or an IMU algorithm.

13. The oral-area positioning method of claim 10, wherein the information corresponding to the plurality of oral areas further comprises moving probabilities between the oral areas, and the oral-area positioning method further comprises:
using the second algorithm to obtain the second position estimation result according to the moving probabilities between the oral areas and the reference image position.

14. The oral-area positioning method of claim 10, wherein the information corresponding to the plurality of oral areas further comprises distance information between the oral areas or angle information between the oral areas.

15. The oral-area positioning method of claim 14, further comprising:
obtaining, by the positioning circuit, shift information between the target image and the reference image according to a third algorithm; and
using the second algorithm to obtain the second position estimation result according to the distance information between the oral areas, the reference image position and the shift information, wherein the third algorithm is an image comparison algorithm or an IMU algorithm.

16. The oral-area positioning method of claim 14, further comprising:
   obtaining, the positioning circuit, angle variance information between the target image and the reference image according to a fourth algorithm; and
   using the second algorithm to obtain the second position estimation result according to the angle information between the oral areas, the reference image position and the angle variance information, wherein the fourth algorithm is an IMU algorithm.

17. The oral-area positioning method of claim 10, further comprising:
   multiplying, by the calculation circuit, the first position estimation result by the second position estimation result to generate the third position estimation result.

18. The oral-area positioning method of claim 10, further comprising:
   multiplying, by the calculation circuit, the first position estimation result by a first weight to generate a first result;
   multiplying, by the calculation circuit, the second position estimation result by a second weight to generate a second result; and
   adding, by the calculation circuit, the first result to the second result to generate the third position estimation result.

* * * * *